(12) United States Patent
Dodds (10) Patent No.: US 6,730,023 B1
(45) Date of Patent: May 4, 2004

(54) ANIMAL GENETIC AND HEALTH PROFILE DATABASE MANAGEMENT

(75) Inventor: W. Jean Dodds, Santa Monica, CA (US)

(73) Assignee: Hemopet, Santa Monica, CA (US)

( * ) Notice: Subject to any disclaimer, the term of this patent is extended or adjusted under 35 U.S.C. 154(b) by 0 days.

(21) Appl. No.: 09/419,192

(22) Filed: Oct. 15, 1999

(51) Int. Cl.$^7$ .................................................. A61B 5/00
(52) U.S. Cl. ....................... 600/300; 702/19; 128/920; 705/1
(58) Field of Search ................................. 600/300–301; 705/2–4; 128/904, 920–925; 434/236–238; 426/232; 702/19

(56) References Cited

U.S. PATENT DOCUMENTS

| | | | | |
|---|---|---|---|---|
| 5,954,640 A | * | 9/1999 | Szabo | 600/300 |
| 6,063,028 A | * | 5/2000 | Luciano | 600/300 |
| 6,287,254 B1 | * | 9/2001 | Dodds | 600/300 |

OTHER PUBLICATIONS

U.S. patent application Ser. No. 09/432,851; filed Nov. 2, 1999; entitled "Animal Health Diagnosis".
Dodds, W. Jean; "More Bumps on the Vaccine Road"; 1999; pp. 715–732.
1997 National Parent Club Canine Health Conference; 'Canine Practice' manual; *The Journal of Canine Medicine and Surgery for the Practitioner*; Jan./Feb. 1998, vol 23; No. 1.
Ru, G.; Terracini, B; and Glickman, L.T.; "Host Related Risk Factors for Canine Osteosarcoma"; *The Veterinary Journal*; 1998; pp. 31–39.
Glickman VMD, DrPH, Larry T.; Glickman MS, MPH, Nita W.; Schellenberg MS, Diana B.; Simpson DVM, Ken; and Lantz DVM, Gary C.; "Multiple Risk Factors for the Gastric Dilatation–Volvulus Syndrome in Dogs: A Practition/Owner Case–Control Study"; 1997; *Journal of the American Animal Hospital Association*; pp. 197–204.
Patroniek, Gary J.; Waters, David J.; and Glickman, Lawrence T.; "Comparative longevity of pet dogs and humans: Implications for gerontology research"; *The Journals of Gerontology*; May 1997; pp. 1–12 and B174–B178.

(List continued on next page.)

*Primary Examiner*—Max F. Hindenburg
*Assistant Examiner*—Michael C Astorino
(74) *Attorney, Agent, or Firm*—Fulbright & Jaworski, L.L.P.

(57) ABSTRACT

A system, method, and apparatus is provided for computerized management of the databases relating to phenotypic health assessment and genomic mapping and genetic screening of animals. Multiple remote users can access a computer network connected with a central database processing resource for managing the data. There is appropriate security and payment of appropriate fees for accessing and retrieving data. Users may input data relating to animal health, lifespan, and genetic background, and obtain reports relating to phenotypic health assessment of a particular animal subject or animal group, and genotypic characteristics of a particular subject or animal group to which this subject belongs. The central computer database processing resource stores phenotypic data and genotypic data relating to animals and analyzes their relationship according to predetermined criteria. The input of data and reporting of data is preferably electronic, or through fax or voice communication. The analysis of the health assessment database and genetic database can be automatic and/or in part manually interpreted by experts related to the central database processing resources.

34 Claims, 7 Drawing Sheets

OTHER PUBLICATIONS

Dodds, W. Jean; "Autoimmune Thyroiditis and Polyglandular Autoimmunity of Purebred Dogs"; *Canine Practice*; Jan./Feb. 1997; vol. 22; No. 1; pp. 18 and 19.

Hancock, Wayne W.; "Chemokines and the Pathogenesis of T Cell–Dependent Immune Responses"; *American Journal of Pathology*; Mar. 1996; vol. 148; No. 2; pp. 681–684.

Dodds, W. Jean; "Estimating Disease Prevalence with Health Surveys and Genetic Screening"; *Advances in Veterinary Science and Comparative Medicine*; 1995; vol. 39; pp. 29–96.

Happ, George M.; "Thyroiditis—A Model Canine Autoimmune Disease"; Department of Biology, University of Vermont, Burlington, Vermont; 1995; pp. 97–139.

Merrill, Jean E. and Jonakait, G. Miller; "Interactions of the nervous and immune systems in development, normal brain homeostasis, and disease"; *The FASEB Journal*; May 1995; vol. 9; pp. 611–618.

Patronek VMD, MS, Gary J. and Glickman VMD, DrPH, Larry T.; "The Epidemiological Approach to Risk Management—Factors Which Increase Chance of Disease"; *Veterinary Forum*; Aug. 1994; pp. 66 and 67.

Jackwood PhD, Mark W.; "Biotechnology and the development of diagnostic tests in veterinary medicine"; *JAVMA*; May 15, 1994; vol. 204; No. 10; pp. 1603–1605.

Dodds, DVM, W. Jean; Raymond BS, Sharon L.; and Brooks DVM; Marjory B.; "Inherited and Acquired von Willebrand's Disease, Part 1"; *Veterinary Practice STAFF*; Jul./Aug. 1993; vol. 5; No. 4; pp 1, 14–17.

Dodds DVM, W. Jean; Raymond BS, Sharon L.; and Brooks DVM; Marjory B.; "Inherited and Acquired von Willebrand's Disease, Part 2"; *Veterinary Practice STAFF*; Sep./Oct. 1993; vol. 5, No. 5; pp. 21–23.

Stefanon DVM, Giovanni; Stefanon PhD, Bruno; and Stefanon DVM, GianGiacomo; "Inhereted and Acquired Canine Bleeding Disorders in Northeastern Italy"; *Canine Practice*; May/Jun. 1993; vol. 18; No. 3; pp. 15–23.

Dodds DVM, W. Jean; "Part 1: An Introduction—Genetically Based Immune Disorders—Autoimmune Diseases"; *Veterinary Practice STAFF*; Jan./Feb. 1992; vol. 4; No. 1; pp. 8–10.

Dodds DVM, W. Jean; "Part 2: Autoimmune Thyroid Disease—Genetically Based Immune Disorders—Autoimmune Diseases"; *Veterinary Practice STAFF*; Mar./Apr. 1992; vol. 4; No. 2; pp. 1, 26–31.

Dodds DVM, W. Jean; "Part 3: Other Autoimmune Diseases—Genetically Based Immune Disorders"; *Veterinary Practice STAFF*; May/Jun. 1992; vol. 4; No. 3; pp. 35–37.

Dodds DVM, W. Jean; "Part 4: Immune Deficiency Diseases—Genetically Based Immune Disorders"; *Veterinary Practice STAFF*; Sep./Oct. 1992; vol. 4; No. 5; pp. 19–21.

Brooks DVM, Marjory; Dodds DVM, W. Jean; and Raymond BS, Sharon L.; "Epidemiologic features of von Willebrand's disease in Doberman Pinschers, Scottish Terriers, and Shetland Sheepdogs: 260 cases (1984–1988)"; *JAVMA*; Apr. 15, 1992; vol. 200; No. 8; pp. 1123–1127, 1966.

Dodds DVM, W. Jean; "Autoimmune Thyroid Disease"; *DOGWORLD*; Apr. 1992, vol. 77; No. 4; pp. 36–40.

Dodds DVM, W. Jean; "Unraveling the autoimmune mystery"; *DOGWORLD*; May 1992; vol. 77; No. 4; pp. 44–48.

Dodds DVM, W. Jean; "Thyroid can alter behavior"; *DOGWORLD*; Oct. 1992; vol. 77; No. 10; pp. 40–42.

Goetzl, Edward J. and Sreedharan, Sunil P.; "Mediators of communication and adaptation in the neuroendocrine and immune systems"; *The FASEB Journal*; Jun. 1992; vol. 6; pp. 2646–2652.

Elmslie DVM, Robyn E; Dow DVM, MS, Steven W.; and Ogilvie DVM, Gregory K.; "Interleukins: Biological Properties and Therapeutic Potential"; *Journal of Veterinary Internal Medicine*; 1991; vol. 5; pp. 283–293.

Raymond BS, Sharon L.; Jones BA, Douglas W.; Brooks DVM; Marjory B.; and Dodds DVM, W. Jean; "Clinical and laboratory features of a severe form of von Willebrand disease in Shetland Sheepdogs"; *JAVMA*; Nov. 15, 1990; vol. 197; No. 10; pp. 1342–1346.

Patterson DVM, DSc, D.F.; Haskins VM, PhD, M.E.; Jezyk VMD, PhD, P.F.; Giger Dr Med Vet, U.; Meyers–Wallen VMD, PhD, V.N.; Aguiree VMD, PhD, G.; Fyfe DVM, J.C.; and Wolfe VMD, PhD, J. H.; "Research on genetic diseases: Reciprocal benefits to animals and man"; *JAVMA*; Nov. 1, 1988; vol. 193; No. 9; pp. 1131–1144.

Jolly, R.D.; Dodds, W.J.; Ruth, G.R; and Trauner, D.B; "Screening for Genetic Diseases: Principles and Practice"; *Advances in Veterinary Science and Comparative Medicine*; 1981; vol. 25; pp. 245–276.

Thompson, R.A. and Lachman, P.J.; "Cytokines and autoimmunology"; *Clinical and Experimental Immunology*; 1994; vol. 96; pp. 1–7.

\* cited by examiner

ANIMAL GENETIC AND HEALTH PROFILE DATABASE MANAGEMENT

TECHNICAL FIELD

This invention relates to a method, system and apparatus for the management of comprehensive and cumulative genetic and health assessment databases in relation to animals worldwide. In particular, the invention relates to a biomformatics system and its implementation in relation to animal biological data.

BACKGROUND OF THE INVENTION

Breeders, owners, and caregivers of animals which can be companions, such as dogs, cats, horses, farm, food, or zoo animals, and wildlife, have a need to understand their physical and biological attributes, genetic makeup, heritable disease, and disorder background, and longevity.

Substantial investments in time, effort and financial resources are made by the breeders, owners, and caregivers of these animals, particularly purebred animals, to characterize their health state and predict their morbidity, mortality and longevity. Resources are separately directed to obtaining information about their genetic background. There is also a need to conduct periodic comprehensive health assessments of animals.

The probability that an individual animal will develop a specific health-related condition in its lifetime is a product of complex interactions between its genetic makeup, environmental influences including diet, and agents of disease (e.g., chemical, physical, or biological) that it encounters. Perhaps the best indicator of overall health of an individual animal or breed is longevity.

The physical attributes, and other descriptive and health assessment information is generally termed in this application as the phenotypic information. Genetic disorder information is termed in this application as the genotypic information. Generally, these are two distinct and differing sets of information.

Phenotype Data

The physical descriptive and health assessment profiles include characteristics such as the physiological, pathological, endocrinological, hematological, epidemiological, behavioral, and immunological data from parameters such as phenotype, breed, lifespan, health history, and presence of infectious diseases and metabolic disorders. All of this is part of the phenotypic information. A health assessment profile of an animal typically relates to a particular subject of the group, as opposed to the group of animals as a whole. Generally, the phenotype is the genetic nature of an organism that is revealed by visible characteristics or measurable performance, in contradistinction to the genotype, which may not be evident without a breeding test or genetic map.

Laboratories having a central database processing resource (CDPR) as well as in-office laboratory equipment at veterinary hospitals or clinics are used for analyzing blood and other biological samples of a subject animal. This is a system for obtaining the phenotypic information. Communication systems are known for connecting these laboratories with veterinary clinics through a telephone and/or fax connection on an automated basis. These systems permit the veterinarian, animal hospital, or other authorized person (collectively or individually termed the "remote user") to receive the health assessment profile and basic descriptive identifying data, namely phenotypic information, of a subject animal from the CDPR. Until recently, it was not possible for the remote user to access the CDPR directly to obtain this phenotypic information of a subject animal.

It is known for the breeder and/or owner of animals, such as purebred companions in the nature of dogs, cats, and horses, or animals of mixed breeding, to obtain health assessments of their animals. The owners obtain these data by submitting blood or other body fluid and tissue samples of their animals, usually through a veterinarian or veterinary clinic, to a laboratory for analysis of the biological, physiological, or pathological condition, namely the physical health of the animal. These data are then reported to the owner through the veterinarian or veterinary clinic. The data also can be stored on the CDPR of the laboratory. Additionally, for each subject animal, the phenotypic data can be stored on a computer storage system at the veterinary clinic or in a computer storage system of the owner and/or breeder. The retrieval of the data can be electronically, by voice, hard copy, or fax as required.

Seeking, obtaining and storing this phenotypic information is driven by the needs of the animal breeder, owner or the agent of the owner and the animal's healthcare provider. This information is of a nature that it is the primary information sought to resolve the clinical, diagnostic, management, and therapeutic needs of an animal subject when the animal is in need of periodic wellness examination, is ill, or is to be restored to a well condition. These data are the essential information resorted to by the clinician in the care of animals.

Genotype Data

The genotypic information relates to genetic mapping, genetic background, and genetic screening databases. This includes data obtained from the pedigree, family history, heritable physical characteristics, genetic screening tests, DNA testing, genomic mapping, and related laboratory assessment of the gene product for known or suspected congenital and heritable traits. In this application, the term "gene product" means the specific phenotypic characteristic(s) resulting from the expression of the genotype, and may include certain specific laboratory test data.

This second aspect of data associated with the animals is the genetic or genotype data or information. These data are typically used to estimate the presence and prevalence of disease or disorder among different breeds or kinds of animals. These data are currently available on some select clinical research databases, in book form, hard copy, or in genetic disease registries.

When retained in a genetic disease registry, the data typically list only those animals that are not affected with or carrying the heritable trait in question. The abnormal or non-normal conditions (affected with or carriers of the heritable trait) are normally the subject of confidential knowledge of a breeder and/or owner, and not the subject of a generally accessible database. This is retained as confidential by the owners either for financial reasons, risk reasons, legal liability reasons, or personal reasons.

The genotypic information typically relates to individual animals, or a group or class of animals and is most often stored manually in a non-CDPR facility. It is not typically stored by veterinarians in a clinical setting, since the genotypic data is a specialist form of data used mainly for cataloging and research of diseases and disorders among animals. It is also not generally available for access to assist in the clinical analysis, diagnosis, and therapeutic management of animals.

This genotypic information, namely the physical characteristics and genetic makeup (pedigree), heritable disorder history, and related health history of animals in the group is usually manually recorded by breeders, owners, and researchers of companion and other valued animals. The genetic constitution of an organism includes genes without visible effects as well as those revealed by the phenotype. It may refer to all the genes or to a single pair of alleles. The genotypic information is transmitted manually to and from persons or local and national genotypic databases maintained for specific disorders, and designed to foster research into diseases and disorders, rather than being readily accessible to users for clinical purposes in the manner of phenotypic data on a CDPR.

Some of the genetic data are available on registries related to specific diseases or disorders, for instance, hip dysplasia, eye conditions, thyroid conditions, and blood conditions. Such disease-specific registries are usually set up either by identifying affected animal breeds, or are indexed by disease or disorder. The genetic information databases are generally closed (kept confidential), but in some cases may be open to researchers or members of groups, associations, and clubs.

Failings of the Existing Systems

To promote better health among animals, which can be animal companions, sport animals, farm animals, and the like, such as canine, feline, equine, bovine, porcine, caprine, ovine, and zoo animals or wildlife, it is important to secure accessible genotypic or genetic information databases. It is also important to be able to relate these genotypic databases to the health assessment profiles or phenotypic databases of particular subject animals.

Many purebred animals are valuable, and so it is important to obtain their descriptive phenotypic information, and periodic health assessment data throughout their lives, and also to incorporate their genotypic information in order to promote and maintain effective high quality and healthy breeding stock, and maximize their lifespan. The phenotype data for an animal include the health assessment profile, breed, and the physical characteristics of the animal. The genotype data include the genetic map, pedigree, family history, genetic screening tests, and disorder and disease characteristics of a particular animal, animal family, line, or group of animals.

There is a need to develop these data in a cumulative, comprehensive, and dynamic system of database management to thereby enhance the health predictability, and longevity of animals.

This type of comprehensive and cumulative database on individual or groups of animals needs to be preserved and shared locally, regionally, nationally, and globally. A mechanism to do this is presently not known due to the various constraints surrounding each of the two types of databases. The phenotype database storage, use, and access is fashioned, formed and structured for use by clinical laboratories and veterinarians. The genotype information is fashioned and structured generally for clinical research and breeder/owner uses as opposed to clinical medical uses.

It is not known to store and/or present phenotypic information and genotypic information as a comprehensive and cumulative assessment of individual animal subjects, families of subjects, breeds of subjects, or species of animals in a computerized format which is available through computer networking to authorized remote users.

Accordingly, there is a need to relate different databases from animals, animal groups or species, in a manner to permit enhancement of the animal kingdom for breeding and growth in a healthy manner with a minimum of disease (reduced morbidity and mortality) and increased longevity.

As the above demonstrates, there is a need for a new database management bioinformatics scheme and relational database, together with computerized networks that manage, analyze, and/or integrate comprehensive and cumulative animal health assessment data and genetic identifier, genomic mapping, and genetic assessment data. A comprehensive approach to animal health and genetic selection or management of animals, and their clinical care is the subject of the present invention.

Current laboratory and research systems and computerization have not achieved this, and nor have communication protocols been used effectively in this technological area to facilitate such a relationship or relational bioinformatics database system for management and dissemination of this comprehensive and cumulative information.

SUMMARY OF THE INVENTION

In light of the above, there is provided by this invention a computerized network system for managing a worldwide database such as to control the phenotypic and genotypic data and information relating to animals, particularly purebred animals.

As such, the invention provides a bioinformatics system for inputting, controlling, analyzing and outputting of a broad range of criteria related to the health, genetic background and longevity of animals. This includes a system concerning phenotype data and genetic data relating to animals. Further, there is provided a system for screening of genetic data and genomic mapping, and integrating the phenotype health assessment data and genetic identifier and assessment data in a CDPR. Moreover, there is provided a system for analyzing the health assessment or phenotypic data with the interrelated genetic or genotypic data. Thereafter, those data and analyses are communicated from the CDPR in a broad range and in a manner that has not previously been possible.

The present invention offers a unique solution to above-described problems by providing an apparatus, method and system, in relation to animals, for performing data analyses of biological specimens from specific subject animals or animal groups in relation to specific subject animal or animal groups of genetic data. The apparatus, method and system comprises a controller for obtaining, inputting, and analyzing biological, physiological, and pathological test data together with genomic mapping and genetic screening data into the CDPR.

The biological, physiological, and pathological data of the subject animal or animal group and the genetic data of the subject animal or animal group are communicated to a remote user as raw data or as related, analyzed biological, physiological, and pathological data and genetic data. The remote user can also appropriately access the CDPR to input data to, or obtain data from, the CDPR.

The CDPR includes at least two databases, one of the databases contains genetic information in relation to animals and the other is a phenotypic database.

The genetic database is either a specific file of a selected animal or a generalized animal database relating to group characteristics, and is cross-relatable with the phenotypic database of particular selected subject animals.

Additionally other databases can be used and cross-related to these databases. The genetic database includes data from selected animals, animal families, animal breeds and/or data related to selected animal diseases and/or disorders. Other databases include those related to genetic markers or maps of animals, databases related to epidemiology, purebred animal ownership, identification registries, and studbook registries.

The phenotype, health profile, or health assessment database contains data which is mostly phenotypic. The genotype database includes data which is in the category of mostly genotype or genetic and which may include a second category of some phenotype data which predicts or manifests the genotype and genetic data. The invention includes relating the phenotypic data to either one or both types of the genotypic data.

Information in the databases are used to build computer driven statistical models to predict the occurrence of specific diseases and longevity for individual animals on a breed-by-breed or family and group basis. Multivariate statistical techniques are used including multiple regression, logistic regression, and Cox proportional hazards. As new diagnostic technology and genomic information become available, the database is continually expanded and the statistical models are updated to enhance predictive ability. This ability to predict the occurrence of disease or disorder is used to develop and evaluate screening programs in veterinary medicine in order to detect disease earlier, thereby improving the outcome and quality of life for animals and their owners. The information is also used to design disease prevention programs based on dietary/environmental modification and selective breeding. The database is also used to explore previously unsuspected relationships between specific diseases such as cancer and diet, vaccination, or chemical exposures.

There is provided means for inputting data into the genetic database and phenotypic database, and other databases, storing the data in these databases, analyzing the data in a relational sense from the different databases, and retrieving the data from these databases, namely the databases which are part of the CDPR.

A further aspect of the invention is the accessibility of the health assessment database and/or genetic database or other databases of the CDPR by the remote user selected on the basis of password, security control, and financial payment such that the data can be transmitted into and from the CDPR by a computer network. Use of selected passwords, encryption systems, and payment systems are employed to facilitate and restrict the flow of data in and/or out of the databases. Alerts can be set up to advise of attempts at unauthorized access to the CDPR. The computer network may conveniently include the Internet.

As required, the data in the CDPR can also be distributed to multiple authorized remote parties, namely third parties for research or other analysis. The invention also includes a method and system for achieving this.

Further aspects of the present invention will become apparent in the course of the following description and by reference to the attached drawings.

DETAILED DESCRIPTION OF THE PREFERRED EMBODIMENT

The present invention will now be described in detail with reference to a few preferred embodiments thereof, as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps have not been described in detail in order to not unnecessarily obscure the present invention.

Genetic Screening and Counseling of Purebred Animals

The common practice to line-breed and inbreed purebred animals facilitates the transmission and recognition of congenital and heritable defects. Large-scale screening programs for the identification of genetically affected and carrier animals are an effective way to discover and eventually control the frequency of these defects within the population at large. Screening programs of this type have been used successfully in humans for many years (e.g. Tay-Sachs disease, phenylketonuria) and more recently have been applied to animals (e.g. mannosidosis in cattle; hip dysplasia, eye, blood and heart diseases in dogs). Genetic screening may be essential to the survival of breeds in which mild or moderately severe defects have been propagated unknowingly for many generations.

It is important that the top-producing sires and foundation dams of a breed be screened for conditions prevalent in that breed or in the species generally, because they represent the major nucleus of genetic material for the current and future decades. Most purebred animals raised today have evolved over the years from a relatively small gene pool. Even. though a particular genetic disorder may initially have been recognized in a specific line or family within a breed, all important breeding stock of the breed need to be screened because their similar genotype evolved from the original restricted gene pool. If this approach is not taken, the frequency of genetic defects in the breed will inevitably increase and have a negative impact on overall health and longevity.

Depending on the mode of inheritance, different approaches may need to be applied for the detection and control of genetic disorders. It is advantageous to be able to select against heterozygotes (carriers) rather than have to eliminate affected individuals from a breeding program once the condition is manifested. Control and elimination of the disease by testing are feasible and reliable in cases where the asymptomatic or carrier state has an expressed phenotypic, biochemical marker (e.g., as measured in a blood, urine or saliva test, electrocardiogram, skin biopsy, eye examination, or hair analysis). Some current examples include testing for bleeding disorders like von Willebrand disease and hemophilia; autoimmune thyroid disease leading to hypothyroidism; the various eye, heart, metabolic enzyme and storage disorders; and the bone and neuromuscular diseases. Coupled with this approach to eliminating undesirable traits is the necessity to evaluate breeding stock regularly for overall soundness, reproductive health and performance, and longevity.

Features Related to Genetic and Other Data Associated with Animals

A. Physical Characteristics of Disease

In the early days when animal breeders began recognizing recurring symptoms of disease states or physical characteristics, the undesirable features of these traits led them to select away from the problems by test mating and eliminating affected animals from the breeding pool. While this remains one way to select against inherited and congenital diseases, more reliable approaches have been implemented by screening for biochemical markers and most recently by using molecular genetic techniques.

A comprehensive worldwide database contains the following information for individual purebred animals:

Host characteristics: age, sex, neuter status, pedigree, height, weight, body mass index, coloration and markings, eye color, etc.

Diet: type and amount of dog and human foods consumed, vitamin and mineral supplements, frequency of feeding. This is used to derive the percentage of calories derived from fat, carbohydrate, and protein.

Medical history: occurrence of diseases, infections, etc., including date of onset, treatment, duration, and outcome, cause of death and method of diagnosis; type and amount of medications used for treatment or prevention of disease; type and frequency of vaccinations.

Personality and temperament: based on previously used personality scales.

Laboratory data: consists of routinely collected blood, serum chemistry tests, urinalysis, etc., as well as laboratory tests performed to screen for or diagnose specific conditions such as immune-mediated thyroiditis, hypothyroidism, cancer, etc.

Special diagnostic test results: include tests for hip dysplasia, congenital eye diseases, congenital heart diseases, blood disorders, and other suspected inherited disorders as tests become available.

Genetic information: derived from the canine genome project as well as tests for specific inherited conditions such as progressive retinal atrophy, hemophilia, and von Willebrand disease.

B. Phenotypic Markers of Disease

While animal breeders (e.g., of purebred dogs) for the most part have endorsed the long standing genetic screening programs for hip dysplasia and blood and eye diseases, emphasis on other genetic disorders has arisen, now that the major infectious, parasitic, nutritional and traumatic diseases have been addressed and controlled to a large extent by modern veterinary medical practice. Furthermore, most animal fanciers become involved in breeding and showing their animals as a hobby rather than a prosperous enterprise as might apply to livestock or the performance racing industry. The intense commitment to this hobby with its attendant social praise for the successful breeder and exhibitor, poses ethical dilemmas when prize-winning animals are identified as carriers of a particular genetic disorder.

For about three decades, veterinary and comparative geneticists have developed and relied upon physical and biochemical markers of specific genetic traits to identify carrier and affected animals. These methods aimed to produce reliable, practical, and affordable tests that would be predictive of the gene product, and therefore the genotype of a particular genetic disorder. To be considered accurate and predictive, retrospective analyses of data developed from these testing programs were compared to the pedigrees of animals being screened as a means of validating the tests. Such genetic screening tests would be considered reliable if they correctly identified animals as having the normal and abnormal genotypes at least 80% of the time.

An important indicator of overall health of an individual animal or breed is longevity. Relationships between a specific health-related condition and an animal's genetic, environmental influences and lifespan have been characterized, in part, for several important diseases of dogs including bone cancer (osteosarcoma) and gastric dilatation-volvulus (GDV).

Osteosarcoma: The risk of osteosarcoma increases with increasing age, increasing weight and increasing height. Compared with the German shepherd breed, the highest risk of osteosarcoma occurs among large and giant breeds, while small breeds have reduced risk. Furthermore, the risk of osteosarcoma is increased two-fold in neutered dogs.

GDV: Factors that increase the risk of GDV in purebred dogs are male gender, being underweight, eating only one meal per day, eating rapidly, and a fearful temperament. Factors that decrease the risk of GDV include a happy temperament and inclusion of table foods in the diet. The lifetime risk of developing GDV in large and giant breed dogs is 20% and 23%, respectively, whereas the lifetime risk of dying of GDV for these breeds is 6%.

Similarly, the comparative longevity of different dog breeds has been described using the age of death and other descriptive characteristics of more than 38,000 dogs that were included in a large veterinary database. Predictable relationships were found between the breed and size of dogs and the average age of death. It was noted that dogs are unique among animal species in having a more than 50-fold difference in adult body size and a corresponding large difference in longevity between the smallest and biggest dog breeds. Since these dog breeds have more than 99% of their genome in common, it suggests that the genetic code for both size and longevity is contained within a very small part of the dog's genome. As mapping of the canine genome progresses, it should be possible to identify not only genes that code for specific diseases such as cancer and GDV, but also for the genes that determine body size and longevity.

C. Genotypic Markers of Disease

Recent advances in molecular genetics have focused on mapping the human genome, and this has stimulated interest in developing parallel genetic maps for animals. For example, it is estimated that a minimum of ten years and several million dollars will be needed to map the canine genome. Once developed, a genetic map provides information about the relative order and placement of genes or specific DNA markers on specific chromosomes. This allows one to locate specific regions on chromosomes where genes of interest are likely to be found. Once a molecular marker is identified close to a specific gene of interest, screening tests for this particular marker can be used to identify individuals carrying or expressing the trait.

Other information in relation to genetic screening and health assessment is contained in the literature references listed at the end of the specification. The contents of these materials are incorporated by reference herein.

Some of the characteristics of animals with which this invention is concerned are the following:

| Animal Characteristics | Mostly Phenotype | Mostly Genotype | Genotype & Some Phenotype (Gene Product) |
|---|---|---|---|
| Species | | | X |
| Purebred | | | X |
| Crossbred | X | | |
| Mixed breed | X | | |
| Size | X | | |
| Weight | X | | |
| Age | X | | |

-continued

| Animal Characteristics | Mostly Phenotype | Mostly Genotype | Genotype & Some Phenotype (Gene Product) |
|---|---|---|---|
| Sex | | | X |
| Lifespan | | | X |
| Body type | X | | |
| Color | | | X |
| Family history | | X | |
| DNA testing | | X | |
| Genomic mapping | | X | |
| Blood type | | X | |
| Thyroid function | X | | |
| von Willebrand factor | | | X |
| Hemophilia | | | X |
| Other bleeding disorders | X | | |
| Glucose | X | | |
| Cholesterol | X | | |
| Alkaline phosphatase | X | | |
| Alanine aminotransferase | X | | |
| Bile acids | X | | |
| Cortisol | X | | |
| Cataracts | X | | |
| Progressive retinal atrophy | | | X |
| Microophthalmia | | | X |
| Dry eye (KCS) | X | | |
| Hip dysplasia | X | | |
| Arthritis | X | | |
| Temperament | X | | |
| Ruptured cruciate ligament | X | | |
| Hemolytic anemia | X | | |
| Urinalysis | X | | |
| Kidney stones | | | X |
| Bloat (gastric dilatation) | | | X |
| Pyoderma | X | | |
| Seborrhea | X | | |
| Sebaceous adenitis | | | X |
| Umbilical hernia | X | | |
| Inguinal hernia | X | | |
| Epilepsy | | | X |
| Heartworm disease | X | | |
| Cardiomyopathy | X | | |
| Patent ductus arteriosus | | | X |
| Immunoglobulin levels | X | | |

In the category of genotype and some phenotype, the phenotype component (measurable gene product) is typically less than 20%.

Overall System

Figure 1:
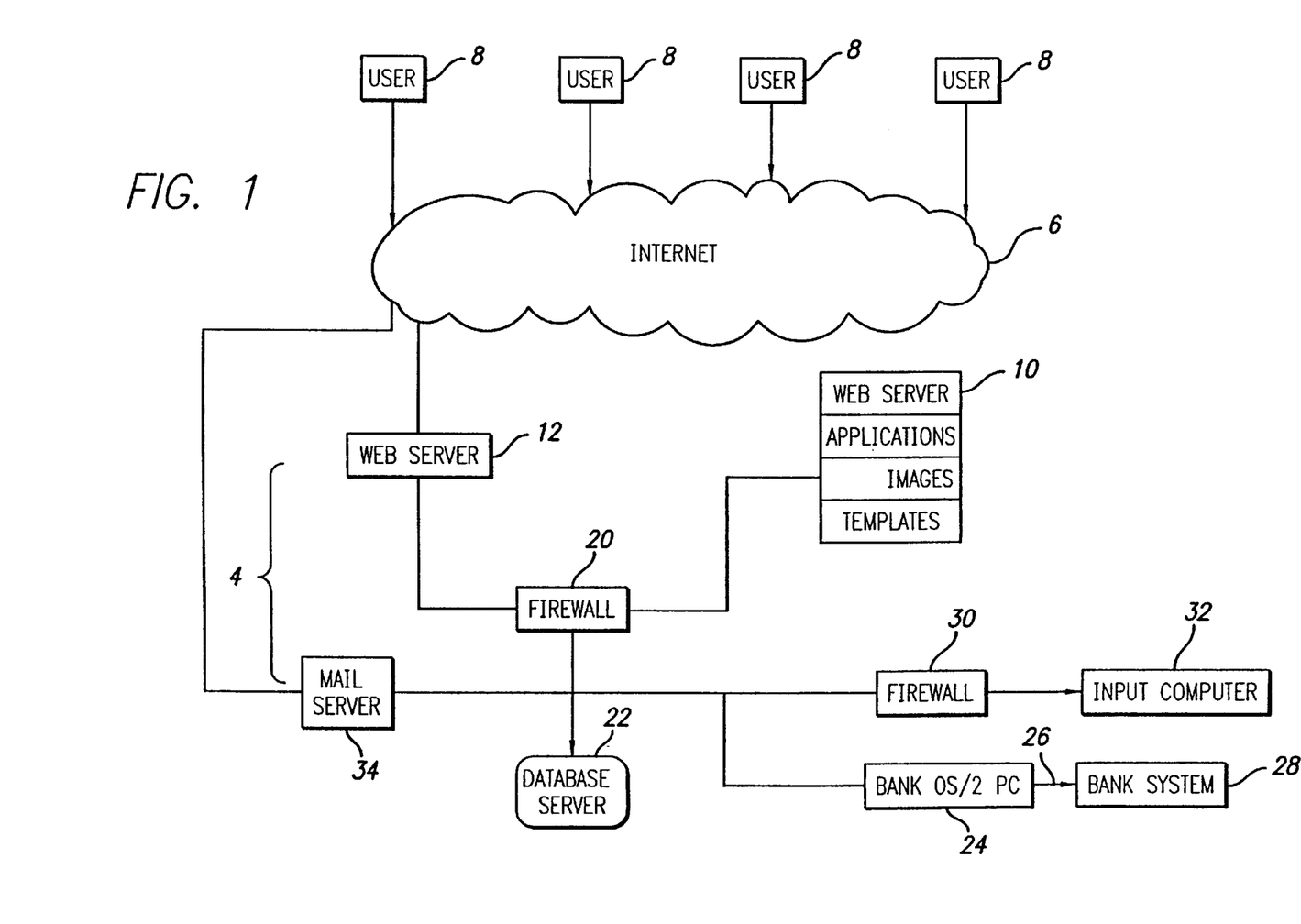
FIG. 1 is an overall view of a web-based system to provide access to a database management system of an animal genetic database and a health assessment database of the invention, in relation to the Internet.

FIG. 1 is an overview of the web-based system to provide access to the invented database management system. With this system multiple users, for instance, remote users 8, access the web site 4 using the Internet 6. Each of the users 8 has a computer terminal with the appropriate software for accessing Internet. The users 8 may be unknown to the web server computers 10 and 12. Each user 8 is allowed to browse the web site and explore how the system functions.

There are several aspects to maintain security of information maintained in the database server 22 and a banking system 28. A firewall 20 prevents any user 8 from accessing any of the components behind the firewall 20. In this way the users 8 have access to the web server computers 10 and 12, but only have access to the database server 22 through the firewall 20. The database server 22 maintains, among other things, various database fields with respect to each of the health profiles of subjects and the genetic information of a subject and groups. The database 22 maintains the services with a designation associated to determine what health assessment data and genetic data can be browsed by the users 8. Each of the web server computers 10 and 12 allow users 8 to view subject and group categories and actual services and data products which are available from the database.

The web server computers 10 and 12 can be identical and can be duplicated as additional load or growth on the system occurs. The web server computers 10 and 12 share the responsibility for servicing the users of the site. This arrangement provides for expandability of the system by merely adding additional web server computers as necessary.

Preferably, the system includes an appropriate computer terminal 24 for interfacing with independent financial institutions which are connected on-line via the serial connection 26 to the financial institution computers 28. This allows automatic real time confirmation of the access of health profile and genetic data services and products. Once a user requires access to a product or service, the user goes through an identification or registration process and the exchange of financial information to allow for credit or debit card payment of the purchase. This is verified, confirmed and authorized by the appropriate bank system institution 28. Confirmation of the purchase or deposit of data, or a service is made by a mail server 34 which sends an E-mail to the user 8 confirming the purchase or deposit. The mail server 34 allows for mail to be received and sent out. Security of the various databases is maintained. Alert messages are generated when an unauthorized access is attempted. Verification messages, authorization messages and confirmation messages are generated as appropriate.

The database server 22 is also designed to interact with an input computer 32 operated by a CDPR. A firewall 30 serves to prevent unauthorized access to the database server 22 or to the input computer 32. The input computer 32 can input health profile data and genetic data to the database, after appropriate access and/or passwords are entered into the system. Similarly, users 8 through their own computers can use appropriate access codes and passwords to access input data to the database server 22. This is tightly controlled for security reasons. The data may only be added to an independent sub-database of the data server 22, and only after scrutiny by the CDPR operator of the database through input computer 32, will this data from users 8 be subsequently added to the main database server 22.

Figure 2:
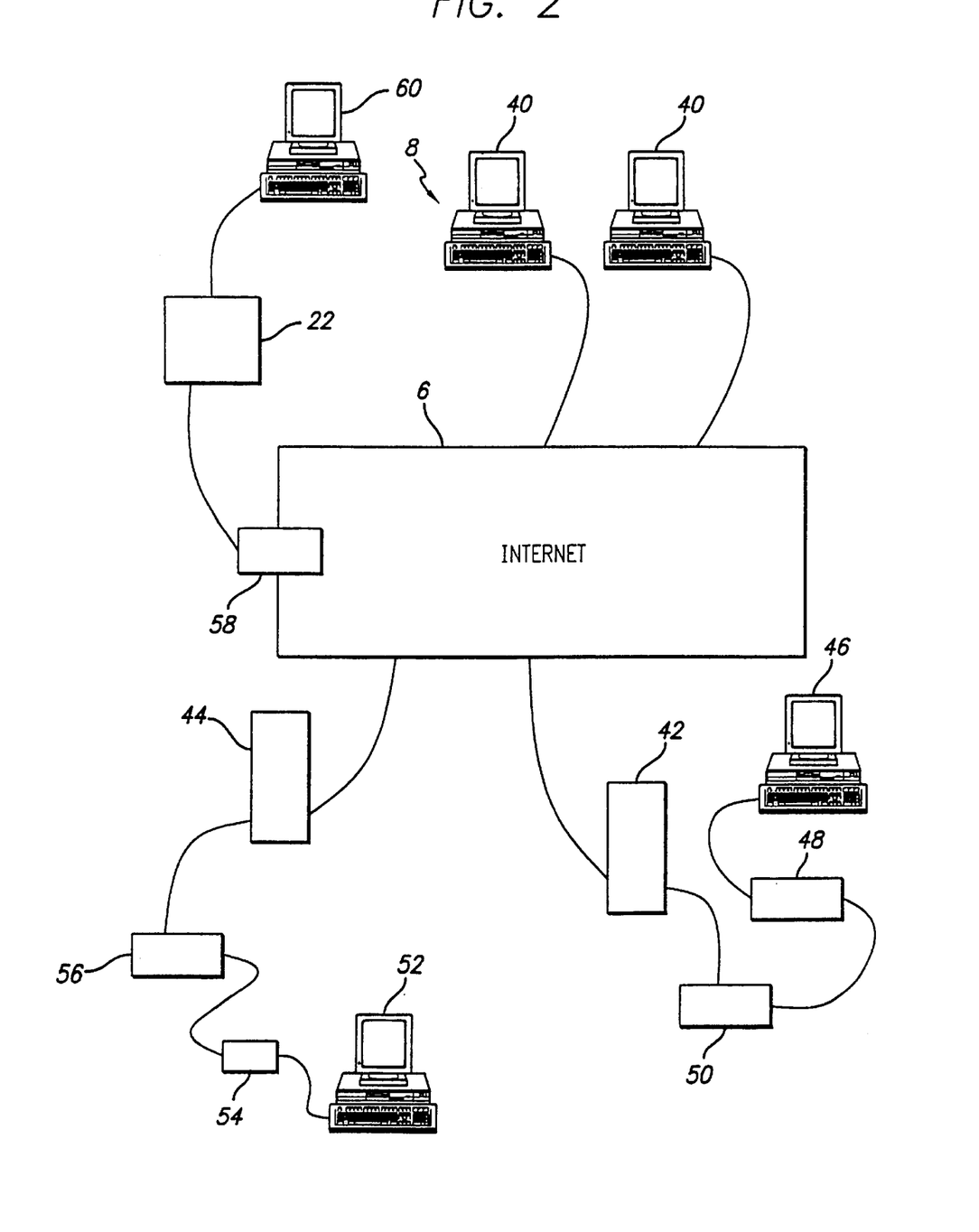
FIG. 2 is a graphical illustration of a computer network, namely the Internet.

FIG. 2 is an illustration of the Internet and its use in the system of the invention. The Internet 6 is a network of millions of interconnected computers 40 including systems owned by Internet providers 42 and information systems 44 such as America Online (TM). Individual or corporate users may establish connections to the Internet in several ways. A user on a home PC 46 may purchase an account through the Internet provider 42. Using a modem 48, the PC user can dial up the Internet provider to connect to a high speed modem 50 which, in turn, provides a full service connection to the Internet. A user 52 may also make a somewhat limited connection to the Internet through a system 20 that provides an Internet gateway connection 54 and 56 to its customers. The database 22 is also connected into the Internet 6 through an appropriate modem or high speed or direct interface 58. The database 22 is operable and maintained by the CDPR operator computer 60. Users of the databases of the invention would access the Internet in an appropriately selected manner.

Figure 3:
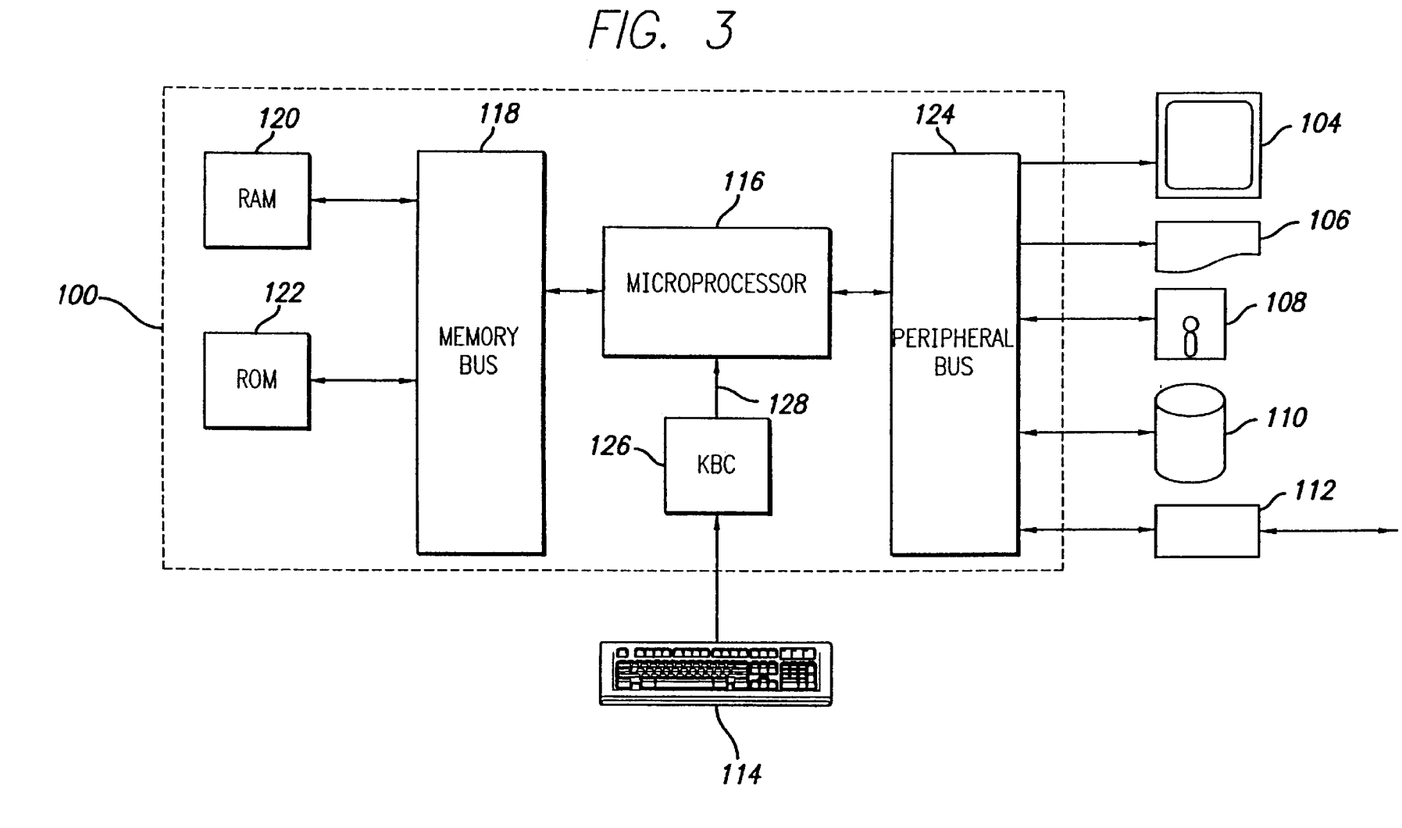
FIG. 3 is a block diagram of an exemplary computer system for practicing various aspects of the invention.

FIG. 3 is a block diagram of an exemplary computer system 100 for practicing various aspects of the invention. The computer system 100 includes a display screen or monitor 104, a printer 106, a disk drive 108, a hard disk drive 110, a network interface 112, and a keyboard 114. The computer system 100 includes a microprocessor 116, a memory bus 118, random access memory (RAM) 129, read only memory (ROM) 122, a peripheral bus 124, and a keyboard controller 126. The computer system 100 can be a personal computer, such as an Apple computer, e.g., an Apple Macintosh (TM), an IBM (TM) personal computer, or a compatible, a workstation computer, such as a Sun Microsystems (TM) or Hewlett-Packard (TM) workstation, or some other type of computer.

Microprocessor 116 is a general purpose digital processor which controls the operation of computer system 100. Microprocessor 116 can be a single-chip processor or can be implemented with multiple components. Using instructions retrieve from memory, the microprocessor 116 controls the reception and manipulation of input data and the output and display of data on output devices.

Memory bus 188 is used by the microprocessor 116 to access RAM 120 and ROM 122. RAM 129 is used by microprocessor 116 as a general storage area and as scratchpad memory, and can also be used to store input data and processed data. ROM 122 can be used to store instructions or program code followed by microprocessor 116 as well as other data.

Peripheral bus 124 is used to access the input, output, and storage devices used by computer system 10. These devices include the display screen 104, printer device 106, disk drive 108, hard disk drive 110, and network interface 112. The keyboard controller 126 is used to receive input from the keyboard 114 and send decoded symbols for each pressed key to microprocessor 116 over bus 128.

The display screen or monitor 104 is an output device that displays images of data provided by microprocessor 116 via peripheral bus 124 or provided by other components in computer system 100. The printer device 106 when operating as a printer provides an image on a sheet of paper or a similar surface. Other output devices such as a plotter, typesetter, etc. can be used in place of, or in addition to the printer device 106.

The disk drive 108 and hard disk drive 110 can be used to store various types of data. The disk drive 108 facilitates transporting such data to other computer systems, and hard disk drive 110 permits fast access to large amounts of stored data.

Microprocessor 116 together with an operating system operate to execute computer code and produce and use data. The computer code and data may reside on RAM 120, ROM 122, or hard disk drive 120. The computer code and data could also reside on a removable program medium and loaded or installed onto computer system 100 when needed. Removable program mediums include, for example, CD-ROM, PC-CARD, floppy disk and magnetic tape.

The network interface circuit 112 is used to send and receive data over a network connected to other computer systems. An interface card or similar device and appropriate software implemented by microprocessor 116 can be used to connect computer system 100 to an existing network and transfer data according to standard protocols. As such he computer system is connectable through an interface device with the Internet 6.

Keyboard 114 is used by a user to input commands and other instructions to computer system 100. Other types of user input devices can also be used in conjunction with the present invention. For example, pointing devices such as a computer mouse, a track ball, a stylus, or a tablet can be used to manipulate a pointer on a screen of a general-purpose computer.

The present invention in relation to the animal database management of data can also be embodied as computer readable code on a computer readable medium. The computer readable medium is any data storage device that can store data which can be thereafter read by a computer system. Examples of the computer readable medium include read-only memory, random-access memory, magnetic data storage devices such as diskettes, and optical data storage devices such as CD-ROMs. The computer readable medium can also be distributed over network coupled computer systems so that the computer readable code is stored and executed in a distributed fashion.

Specific System

Figure 4:
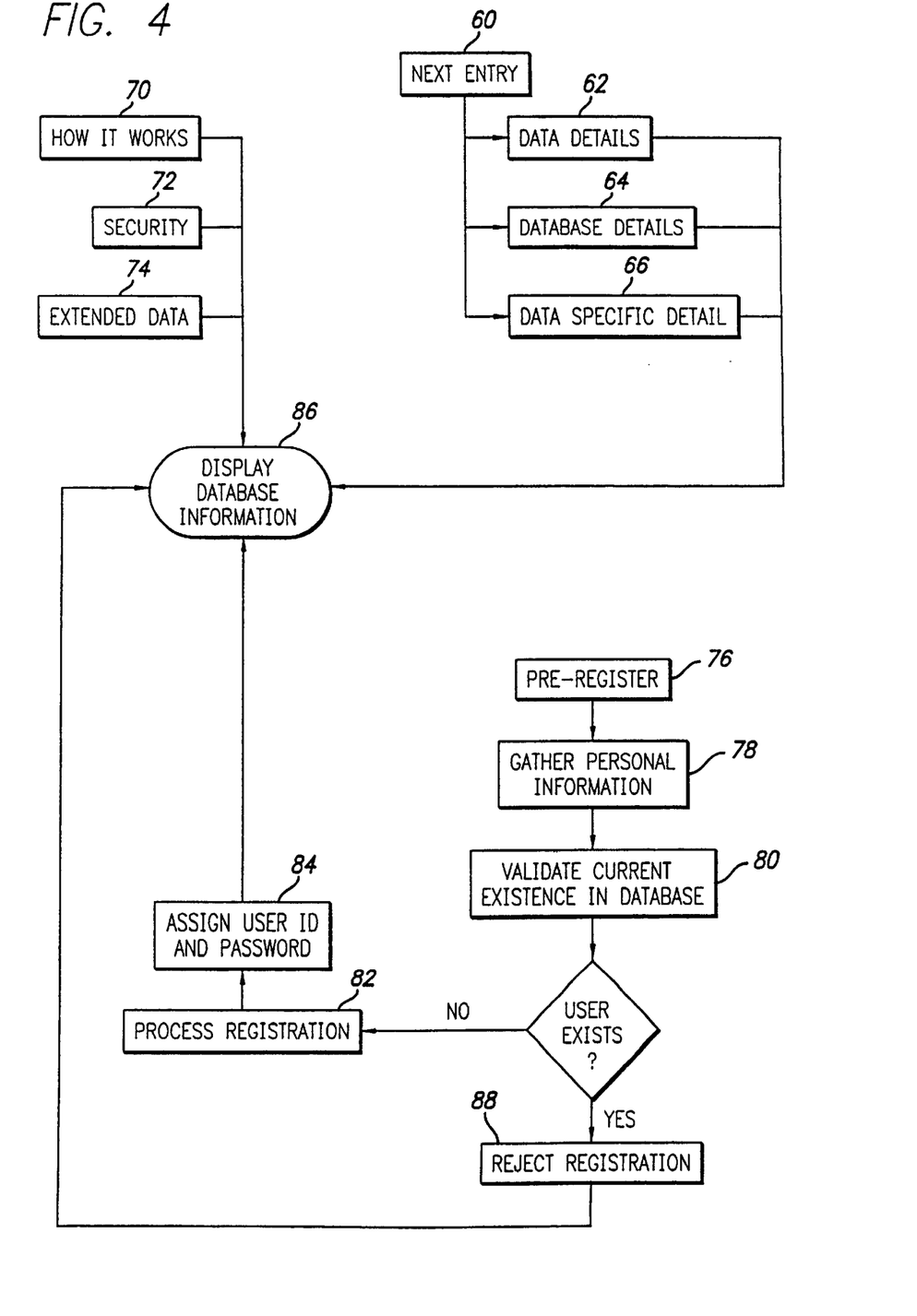
FIG. 4 is a view of a browser for the database management system for accessing an animal genetic database and a health assessment database of the invention.

FIG. 4 illustrates a browser system for use with the database system of the invention. A browser goes through a number of preliminary screens and logic steps, and reaches a screen 60 entitled "Next Entry". This screen provides data details or information generally indicated as 62. Clicking on any of these categories allows the user to review database details 64, data specific details as generally indicated by 66. In this way, the user can index through a number of screens to get information regarding the different databases of the system. In addition, clicking on any of the triggers 70, 72, 74 and 76 is possible. These correspond to HOW IT WORKS, SECURITY, EXTENDED DATA and PRE-REGISTRATION. Clicking on trigger 70 provides the user with information on how the process works, explains the system, and provides details on how the user can participate in the database and obtain data or input data. Clicking on trigger 72 provides details regarding security of the system and automatic payment. In some cases, products and services are offered with extended data and clicking on trigger 74 which can provide details of the extended data and explains that this may only be available on certain services or products.

Trigger 76 allows a user to pre-register and obtain user ID number. This ID number is combined with financial information retained in the database in an encrypted form. The pre-registration trigger 76 follows with step 78 which is to gather personal information such as credit card number and expiry date to allow for automatic payment. Step 80 is to validate a current existence in the database, if this occurs. With a negative answer, the user is directed into a registration process indicate as 82. A user ID is assigned and a password is entered. This information is maintained in a portion of the database 22. At 84 the user is provided a screen identifying the user ID at screen 86. If the user already exists, the registration process is rejected at 88 and the user is advised of the information at the display 86. The screen at 86 would also represent the information which is available in the database 22.

Figure 5:
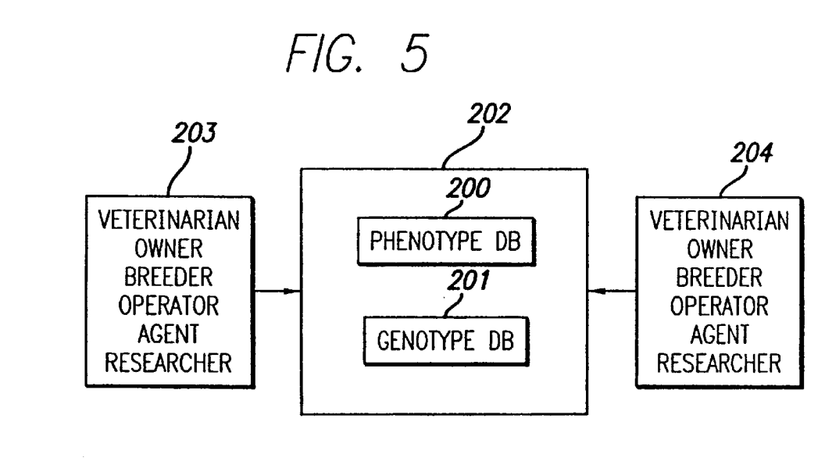
FIG. 5 is a basic flow diagram illustrating an exemplary process by which an operator of a CDPR receives and transmits data relating to health assessment and genetic information.

In FIG. 5 there is shown a basic block diagram of the components making up the CDPR. There is the phenotype database or physical health database 200 and a genotype database or genetic information database 201. These are contained in part of the overall CDPR database 202. User input 203 can be obtained from a remote user such as a veterinarian, owner, breeder, or the operator of the database, an agent or researcher. The output from the database 204 could be to the veterinarian, owner, breeder, operator, agent or researcher.

Figure 6:
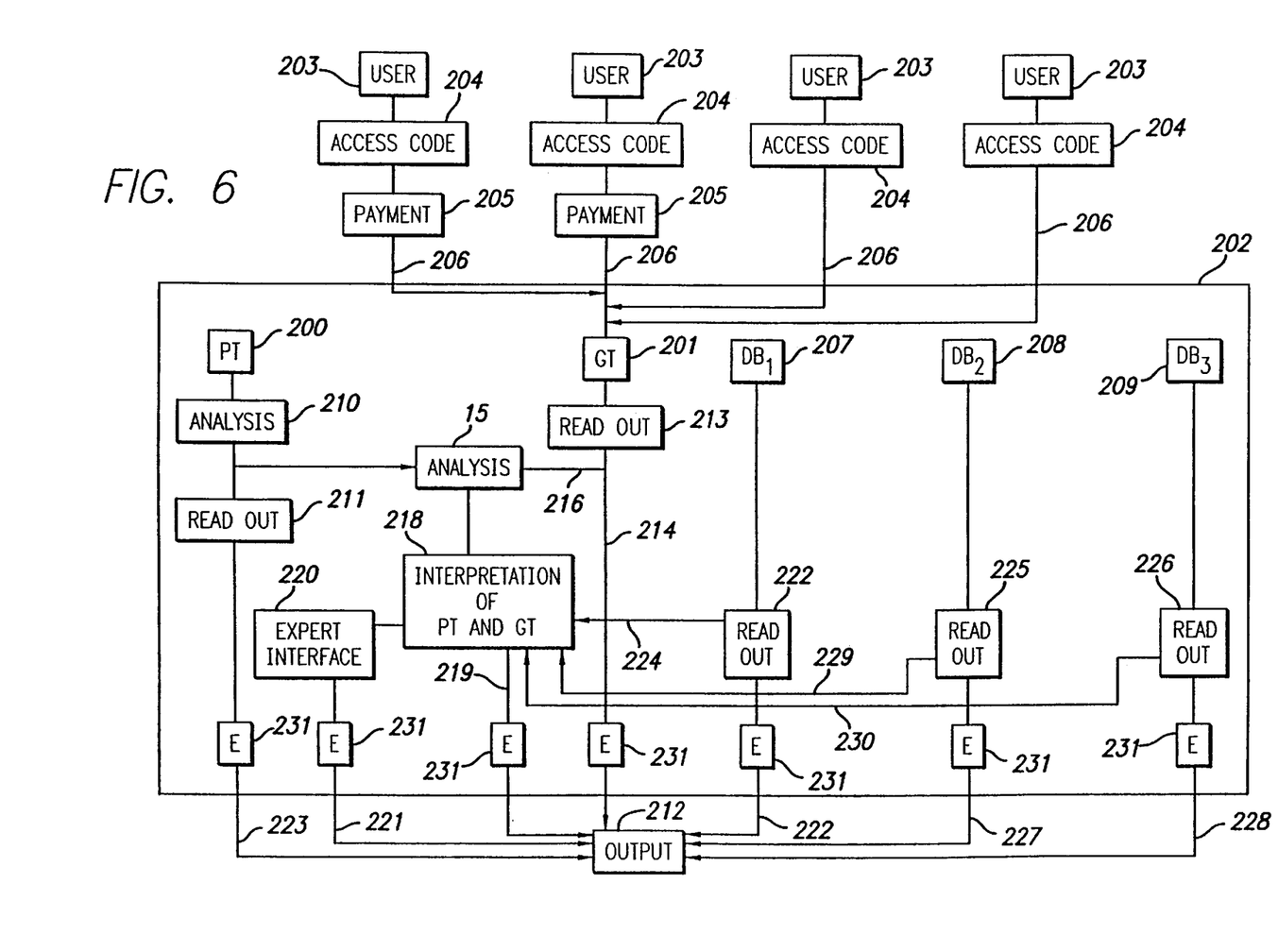
FIG. 6 is a detailed flow diagram of the system steps employed in one embodiment of the present invention wherein a remote user accesses and outputs data.

FIG. 6 shows a relationship for retrieving data from the database 202. The user 8 is represented here as a veterinarian, owner, breeder, operator, or researcher 203 who accesses the CDPR 202 accesses a first screen through a computer network 6 which inquires about information about the user. An access request message is sent, and an appropriate access enabling message is transmitted. The user 203 can obtain partial or full access to the CDPR 202 according to the scale of authority given to the user 203 to access data. There is a computer program system 205 to ensure that payment is made as appropriate before access to the CDPR 202 is granted. In some situations, the appropriate access code 204 can permit bypassing the payment requirement 205 as indicated by line 206. Payments 205 through the computer program can be effected by a credit card entry and automatic transfer to a financial institution on behalf of the operator of the CDPR 202. Such payment for access to the database is effected by a system which is well known in the art. The financial institution will appropriately credit the operator of the CDPR 202 in a financial manner as established between the operator and the financial institution.

Within the CDPR 201 there is the ability to access the physical health phenotype database 200, the genotype database 201, and other databases 207, 208 and 209, respectively. The phenotypic and genotypic information together with other database information can be presented on a single screen or monitor or other viewing means, for instance, hard copy format. The access therefore can be to multiple databases contained within the CDPR 202. After accessing the physical health database 200, the user obtains an analysis report from module 210. The user is then able to read the analysis as indicated by 211 and output the analysis from the read-out 211 as indicated by output 212. The output 212 can be a computer screen read-out, fax or voice information.

The physical health or phenotype database 200 is subject or group specific. In other words, the data obtained in that database is specific to a particular animal or animal group (breed, family, species, etc.) which has been the subject of a laboratory or research biological examination such that fluid or tissue samples have been subject to analysis in one or more laboratory or research environments. These biological reports can include those from specimens of blood, urine, other body fluids, skin, eyes, skeletal and other tissues. The PT database 200 has the ability to store the subject specific information as required within the CDPR 202.

The genotype specific or genetic disorder or disease data is retained in the database 201 within the CDPR database 202. This data is either subject specific, family specific, breed specific, species specific, disorder specific, or disease specific, and is group or subject specific. The user can access the genotype database 201 and obtain a read-out 213 which can then be transmitted along line 214 to an output 212 in the same manner that the physical health assessment is obtained as an output.

In an alternative approach, the reader can request an analysis 215 from the genotype database as indicated by line 216. This analysis can receive data along line 217 from the analysis information of the physical health assessment. Interpretation of the PT and GT can be obtained as indicated by 218, and this can then be outputted as indicated along line 219. The interpretation of PT and GT 218 can be performed by an algorithm relating to the coefficients and predictability of information relating to disorders, disease and longevity when considering the data from the two databases PT 200 and GT 201. This can be done automatically and outputted along line 219, or there can be an expert interface 220 using skilled personnel to interpret the data of block 218, and this can, in turn, be outputted along line 221 to the output 212.

Database 207 can be a genetic marker database, and the information from that database can be directly input into the output through a read-out 222 and 223 to the output 212. Alternatively, the data from database 207 can be added to the interpretation section 218 of the physical health and genetic information by directing the data along line 224. This data can then be made the subject of the output along the line 219 and 221 as required.

Similarly other databases 208, 209, respectively, have read-outs 225 and 226 which can be directly coupled along lines 227 and 228 to the output, or can be directed optionally along lines 229 and 230 to the interpretation module 218. It can then be the subject of interpretation for an expert interface 220 review which is, in turn, made the subject of the output 219 and 221.

In each of the output lines 219, 221, 222, 223, 227, 228, and 214 there is also provided an encryption program 231 which can be optionally used in the system. The output 212 can include paper, electronic, or voice read-out as is required.

In this manner, the output 212 provides a compilation which combines the physical health and genetic information relating to a subject, the breed, disease, disorder and lifespan, thereby enabling the receiver of the output 212 to use the compiled information in a manner to facilitate breeding criteria which can be important in relation to animals which are usually inbred or line bred. The information can also be used to facilitate on-going monitoring of particular subject animals. The data from this system can be used to manipulate and regulate breeding, health, and longevity effectively among animals.

Figure 7:
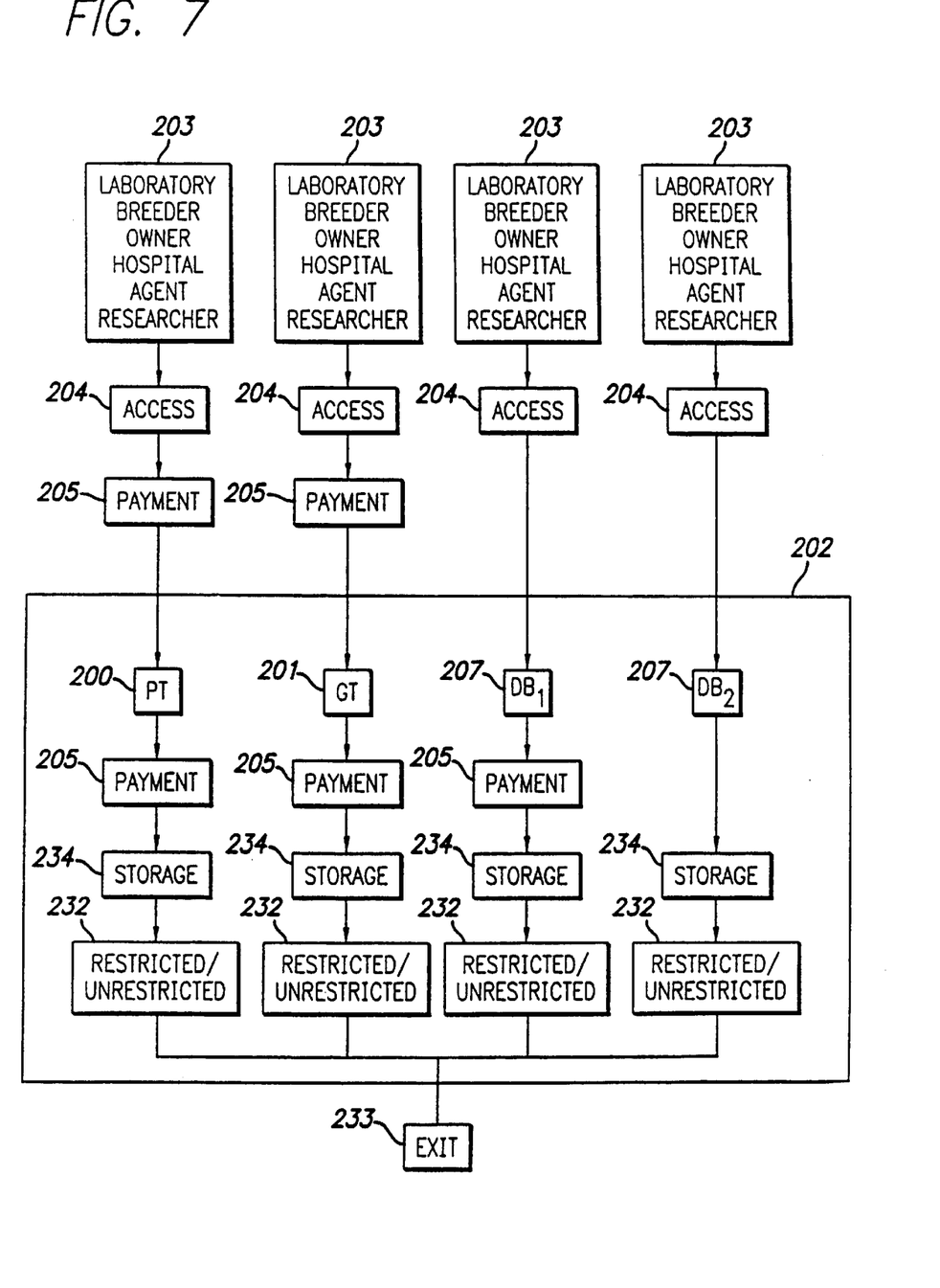
FIG. 7 is a detailed flow diagram of the methods and steps employed by a remote user to add data to the database.

The system of the invention is further described with regard to FIG. 7 which is a system for inputting data to the CDPR 202. Here multiple users 203, which can be a remote user such as a laboratory, a breeder. an owner, hospital, agent, or an operator of the CDPR 202 accesses the system through module 204 which, in turn, accesses the CDPR 202. Appropriate access request and access enable messages are sent. Within the CDPR 202 there is a physical health or phenotype module 200, a genetic or genotype data module 201, and other database modules 207, etc. After accessing the CDPR 202, additional data can be added to the modules 200, 201, 207, etc. through any of the users 203, if authorized. Depositing data into each of the modules 200, 201 and 207 can optionally require the payment to the operator of the CDPR 202 as is indicated by block 205. This system can function in the same manner as the retrieval of data from CDPR 202.

The stored data in each of the blocks 200, 201, and 207 can be set up as indicated by block 232 in a manner which is restricted or unrestricted to selected users 203. This may be necessary according to the protocols governing the inputted data to the different databases. In some cases, the waiving of deposit fees is made in the interest of freedom of the database to subsequent users who wish to retrieve data from the database. After storage of the data as indicated by block 234, the user 203 exits CDPR 202 as indicated by block 233.

As is apparent, the physical health or phenotype profile of subject animals is dynamic and grows as more data is added into the system. Likewise, the genetic genotype database also grows as increasing research of particular subjects, breeds, and the like is obtained. The deposit of new information into the CDPR 202 is regulated in a manner that the data cannot distort the databases 202 in an in appropriate manner. Likewise, users 203 cannot access the secured databases within CDPR 202 in an inappropriate manner.

Different algorithms regulate the relationship between the health profile, the genetic data, and other data relating to animals. These algorithms determine the probabilities, possibilities, and likelihood of disorders and disease in subject animals and offspring animals. They are used as predictors of the future evolvement of health of the animal. Examples of Inter-Relationship and Algorithm Inter-Relationship of the Phenotype and Genotype Data Bases In one example the genetic influence on behavior and behavioral disorders accounts for less than half of the phenotypic expression of behavior and behavioral differences. However, behavior is the most complex phenotype, because it reflects not only the functioning of the whole being but also is dynamic and changes in response to environmental influences. These results are most dramatically seen in purebred animals because they have been inbred and line-bred to select for a particular behavior and conformation, even though the genotype of purebred breeds shows almost no variation over 100 years. Examples of this are all the different purebred dog breeds which currently exist, and have widely disparate size, weight, temperament and lifespans.

Accordingly, if the results of a mostly phenotypic database indicate abnormal thyroid function, then by relating this to the mostly genotypic and combined database categories of breed, age and sex, it is possible to determine whether the subject has or does not have heritable thyroid disease, or is likely to develop this condition within a predicted period of time.

Similarly, if the phenotypic database indicates elevated blood and urine glucose levels, then by relating this to the genotypic and combined database categories of weight, age, sex, breed and reproductive history, it is possible to determine that the subject has diabetes that is likely to be of an heritable basis.

Another example relates the phenotypic database indicating low blood von Willebrand factor level to the genotypic and combined database categories of breed, age, sex, and clinical and family history, whereby it is possible to determine whether the subject has the inherited or acquired form of von Willebrand disease.

Analyzing the data from the CDPR 102 in the manner of the present invention permits for genetic screening, health assessment profiling, and the diagnostic, prophylactic, and therapeutic management of animals.

An exemplary server performs all the operations of a conventional database system and performs additional operations in accordance with the present invention as has been discussed. The server includes a central processing unit (CPU) together with associated memory for processing information about different animals species and history. The inquiries concern animals species and history and inquiries and requests for health profiling and genetic information, and providing health profiles and genetic information. The CPU is coupled to the database and to users via a communications port. The CPU is also coupled to an electronic mail processor for processing and storing (in a storage device) e-mail messages transmitted between the CPU and various agents, users and the like. The CPU is further coupled to a data storage device. A data storage device may include a variety of the databases. The system permits for the requesting, storing and providing of data with respect to animal phenotypic information and genetic information. The format and content of the databases have been discussed in detail.

Figure 8:
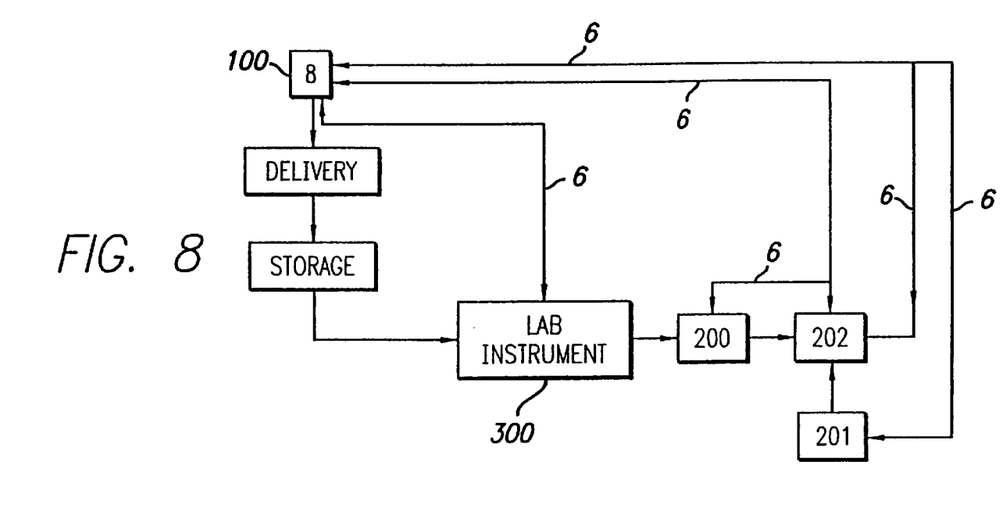
FIG. 8 is a flow chart illustrating an exemplary process by which the laboratory dynamically contributes, transmits and receives data associated with health assessment and genetic data to the CDPR.

FIG. 8 presents an overview of the laboratory instruments apparatus, system, and method operable with the present invention in relation to a CDPR 202. The present invention allows access by remote users with computers or processors 100 to receive and access data on specimens. Using the Internet 6 or other computer network or communication link capability, the remote user 8 sends a message to request access to the services provided by the laboratory or operator which has a CDPR 202. If access to the CDPR 202 is granted, a message is sent to the remote user computers 100. This message includes instructions enabling the remote user 8 to define and access data stored in the CDPR 202.

In one form of the invention, the desired data is based on the submission of test specimens of a specific animal to the laboratory. In some other cases health profile test data 200 can be inputted into the CDPR 202 having the genetic database 201. The CDPR 202 can perform an analysis and correlation between the health profile database 200 and the genetic database 201.

Using the communications link, the remote user 8 communicates with the laboratory or the CDPR 202. Specimens can be packaged and physically transported to the laboratory site via commercially available common carriers, such as the postal service or courier services. When the packages arrive, the laboratory places them in storage, or the tests are performed. Instruments 300 perform the tests to obtain data as specified by the remote user 8. The biohazardous samples can be disposed of a waste material. The test results, or output is provided as part of a health profile database 200 of the CDPR 202 and is available to the remote user 8.

If desired, the remote user 8 can arrange to have the data stored in the CDPR 202, made available to other remote users 8. The remote user 8 can also request the laboratory to perform analysis on the health profile data 200 generated.

In one embodiment, the communications link is a computer network and the message transfer modality is, for instance, the Internet 6, and/or an Intranet and/or an Extranet. The network systems are particularly suited to the application described herein since it offers global or widespread accessibility and high speed data transfer of large amounts of information.

A security unit allows remote users to designate who has permission to view or use their data. Feasible options for these information management requirements include: access by the submitting remote users only, access by certain designated researchers and collaborators, time-embargoed data followed by wider access, and unrestricted access by all. A commerce unit can implement functions related to the business aspects of the CDPR facility, including billing, inventory management of support materials.

A multimedia unit comprises means to store, manipulate, and present audio, graphical, video information. This information may include a video explaining how the CDPR is used, a visual depiction of the data, methodology, or a comment regarding the background of the data. The multimedia unit may also implement subscription functions, so that updated data automatically provided to remote users or other interested parties.

The operations performed by the present invention begins when the controller receives an access request message from the remote user via a communication link. Using information in the access request message and any other available information, the controller determines if the remote user is authorized to access the CDPR 202. If so, an access enabling message is transmitted from the controller to the remote user 8. The access enabling message can comprise a set of computer instructions transmitted over the Internet 6 which is downloaded into the remote user memory for execution by the remote user processor. These instructions may be enabling, that is, they may allow direct communication between the remote user 8 and the CDPR 202 with no further need for the controller. In another embodiment, the access enabling message may simply comprise a password or other enabling message which allows the remote user 8 to proceed. The remote user 8 can access or submit data to the CDPR 202 according to different protocols and regimes and security arrangements.

Conclusion

As the above demonstrates, there is a need for providing data analysis and dissemination services to a wide variety of globally-distributed remote users. There is a need for providing a system for inputting, storing and retrieving data related to animal health assessment and genetics in a manner which permits for the effective use of this information.

The system also permits for the access to the genetic and/or phenotype data through a password and a system whereby access to the data generates a fee. This system permits for the access or to provide data with regard to credit cards or the like to ensure that the fee is transmitted automatically to a banking system for the account of the database when such data is accessed.

This system also provides for a situation wherein payments can be made by credit card for requests to perform health assessment profiles and secure genomic mapping and genetic screening information. Such bioinformatics system can also permit for the automatic payment for such services and products to the banking system of the database or laboratory. As such, the database may require that the payments be guaranteed, for instance by supplying a credit card number with a request for performance of services and a product, and for the retrieval of such data.

A user can submit a request to the database in any number of ways. For example, the request can be submitted via on-line direct connection, namely through a computer network such as the Internet. An intermediate researcher such as a veterinarian or scientist other than the owner could also submit the request on behalf of the owner using the e-mail capabilities of the central database system. Alternatively, the user can submit the data via an interactive voice response unit coupled to the database system of the supplier. In some situations, the database supplier can decide whether to supply the health assessment information and/or genomic mapping and genetic screening information based on the criteria of the user or its intermediary agent. Such user or intermediary agent can be notified of the decision via the interactive response unit or a live operator.

The user or agent can log into the database system and obtain the necessary records relating to an animal physical health and/or genetic ancestry or offspring. The database system can transmit in real time or on a periodic basis as determined, thereby, providing information regarding the health assessment or the genetic background and forward this information to the user and/or its intermediary agent.

The data storage devices of the invention include a variety of databases including a database relating to the phenotypic data of a particular species, a database relating to health assessment or other phenotypic data of particular animals in a particular species, and genetic characteristics of different species and different family trees relating to different species. The family trees would contain information including the origin, genomic map, and parental lines of a species and records of health and performance of a species. These databases are interrelated in an analytical manner and in accordance with different algorithms of permutations and probabilities to facilitate useful output information based on the combination of data in the genotypic and the phenotypic databases, and the selected databases.

Many other examples of the invention exist, each differing from others in matters of detail only. The invention is to be determined solely by the following claims.

REFERENCES

Dodds, W. J. More Bumps on the Vaccine Road. Adv. Vet. Med. 41:715–732, 1999.
Canine Health Conference 1997, National Parent Club of American Kennel Club/AKC Canine Health Foundation. Can. Pract. 23(1):1–56, 1998.
Ru, G, Terracini, B, Glickman, L. Host Related Risk Factors for Canine Osteosarcoma. Vet. J. 156:31–39, 1998.
Glickman, L, Glickman, N, Schellenberg, D, et al. Multiple Risk Factors for the Gastric Dilatation-Volvulus Syndrome in Dogs: A Practitioner/Owner Case-Control Study. J. Am. Anim. Hosp. Assoc. 33;197–204, 1997.
Patronek, G, Waters, D, Glickman, L. Comparative Longevity of Pet Dogs and Humans: Implications for Gerontology Research. J. Gerontol. 52A:B171–178, 1997.
Dodds, W. J. Autoimmune Thyroiditis and Polyglandular Autoimmunity of Purebred Dogs. Can. Pract. 22 (1): 18–19, 1997.
Dodds, W. J. Estimating Disease Prevalence with Health Surveys and Genetic Screening. Adv. Vet. Sci. Comp. Med. 39: 29–96, 1995.
Dodds, W. J., Raymond, S. L., Brooks, M. B. Inherited and Acquired von Willebrand's Disease. Parts 1–2. Vet. Pract. STAFF 5(4–5): 1, 14–17; 21–23, 1993.
Stefanon, G., Stefanon, B., Stefanon, G. G., Dodds, W. J. Inherited and Acquired Bleeding Disorders in Northeastern Italy. Can. Pract. 18(3); 15–23, 1993.
Dodds, W. J. Genetically Based Immune Disorders: Autoimmune and Other Diseases. Parts 1–3. Vet. Pract. STAFF 4(1–3): 8–10, 1, 26–31; 35–37, 1992.
Dodds, W. J. Genetically Based Immune Disorders: Immune Deficiency Diseases. Vet. Pract. STAFF 4(5); 19–21, 1992.
Brooks, M. B., Dodds, W. J., and Raymond, S. L. Epidemiologic Features of von Willebrand's Disease in Doberman Pinschers, Scottish Terriers and Shetland Sheepdogs. 260 cases (1984–1988). J. Am. Vet. Med. Assoc. 200:1123–1127, 1992.
Dodds, W. J. Autoimmune Thyroid Disease. Dog World 77(4): 36–40, 1992.
Dodds, W. J. Unraveling the Autoimmune Mystery. Dog World 77(5): 44–48, 1992.
Dodds, W. J. Thyroid Can Alter Behavior. Dog World 77(10):40–42, 1992.
Raymond, S. L., Jones, D. W., Brooks, M. B., Dodds, W. J. Clinical and Laboratory Features of a Severe Form of von Willebrand's Disease in Shetland Sheepdogs. J. Am. Vet. Med. Assoc. 197:1342–1346, 1990.
Jolly, R. D., Dodds, W. J., Ruth, G. R., Trauner, D. B. Screening for Genetic Diseases: Principles and Practice. Adv. Vet. Sci. Comp. Med. 25: 245–276, 1981.

What is claimed is:

1. A method of communicating phenotypic and genotypic data related to a non-human animal, the data communication being between a central database processing resource and at least one remote user, the method comprising the steps of:
   receiving an access request message from a remote user via a communications link;
   transmitting an access enabling message to the remote user via the communications link wherein the remote user is authorized to access the database, the access enabling message permitting the remote user to access the database and access designated data from the database, the data in the database including phenotypic and genotypic data related to the animal;
   analyzing the phenotypic and genotypic data related to the animal;
   compiling a report based on the analysis of the phenotypic and genotypic data of the animal; and
   transmitting the compiled report of the phenotypic and genotypic data of the animal to the remote user.

2. The method of claim 1, comprising the steps of verifying that the access to the database is authorized.

3. The method of claim 1, including periodically updating the database with at least one phenoyypic or genotypic data about the animal.

4. The method of claim 1, including analyzing the health assessment data of an animal and the genetic data related to that animal, and providing the report to the remote user based on the analysis the health assessment data of the animal and the genetic data.

5. The method of claim 1, comprising the step of storing the report in the central database resource.

6. The method of claim 1, including controlling access to the central database resource, and wherein data in the database is accessible to selected multiple remote clients.

7. The method of claim 6, including the step of verifying that selected remote clients are authorized to access the database or selected data in the database.

8. The method of claim 1, including interpreting the phenotypic and genotypic data the animal thereby predicting health, disease probabilities, disorder probabilities or longevity of the animal.

9. The method of claim 1, including sending an access request message from the remote user via a communications link, and the communications link is selectively a computer network.

10. The method of claim 9, wherein the computer network includes the Internet.

11. The method of claim 1, including receiving a biological specimen result of the animal, storing, retrieving, comparing, and analyzing the biological specimen thereby obtaining phenotypic data of the animal.

12. The method of claim 1, including encrypting the phenotypic and genotypic data.

13. The method of claim 1, including the steps of communicating between a remote user and the central database processing resource through a computer network, providing credit card information of the remote user prior to providing at least one of phenotypic or genotypic data of the animal and transferring such data to the remote user after charging a credit card for such data.

14. The method of claim 1, including transferring money electronically via a telecommunications line between respective financial entities related to the remote user and to an operator of the central database, and, after transfer of money electronically, providing data from the central database to the remote user.

15. A method of viewing phenotypic and genotypic data related to a non-human animal comprising the steps of:
   viewing, using a computer, both phenotypic data and genotypic data for a non-human animal;
   receiving in a database of a central database processing resource related to the computer, data relating to the phenotype data of the animal and receiving in the database of the central data processing resource, genotypic data relating to the breed of the animal and genetic background of the animal;
   analyzing, using a computer, the phenotypic data and the genotypic data based on predetermined characteristics; and
   reporting the analysis of the phenotypic data and genotypic data.

16. The method of claim 15, wherein a remote user of a database including phenotypic data and genotypic data pays for at least one of an analysis of phenotypic or genotypic data through a computer network, and including submitting the report to a remote user after receipt of the payment.

17. The method of claim 15, including submitting a health assessment to a database related to the computer, the health assessment being selected by a remote user.

18. The method of claim 15, wherein the reporting is to a remote user, the remote user being at a site removed from a central database related to the computer and using a communication link between the central database and the remote user, the communication link including an Internet link.

19. Apparatus for communicating phenotypic and genotypic data related to a non-human animal, comprising
   a computer communication network for data communication being between a central database processing resource and at least one remote user,
   means for receiving an access request message from a remote user via the communications link;
   means for transmitting an access enabling message to the remote user via the communications link wherein the remote user is authorized to access the database, the access enabling message permitting the remote user to access the database and access designated data from the database, the data in the database including phenotypic and genotypic data related to the animal;
   means for analyzing the phenotypic and genotypic data related to the animal;
   means for compiling a report based on the analysis phenotypic and genotypic data of the animal; and
   means for transmitting the compiled report of the phenotypic and genotypic data of the animal to the remote user.

20. The apparatus of claim 19, comprising means for verifying that the access to the database is authorized.

21. The apparatus of claim 19, including means for analyzing the health assessment data of an animal and the genetic data related to the animal, and means for providing the report to the remote user based on the analysis the health assessment data of the animal and the genetic data.

22. The apparatus of claim 19, comprising means for storing the report in the central database processing resource.

23. The apparatus of claim 19, including means for controlling access to the central database processing resource to selected multiple remote clients.

24. The apparatus of claim 19, including means for interpreting the phenotypic and genotypic data, and means to permit an analysis of the interpreted data thereby predicting health, disease probabilities, disorder probabilities or longevity of the animal.

25. The apparatus of claim 19, including means of communicating between a remote user and the central database processing resource through a computer network, means for providing credit card information of the remote user prior to providing at least one of phenotypic or genotypic data and transferring such data to the remote user after charging a credit card for such data.

26. Apparatus comprising:
   a screen for monitoring, using a computer both phenotypic data and genotypic data for a non-human animal;
   a computer for analyzing the phenotypic and the genotypic data based on predetermined characteristics;
   a means for receiving in a database of a central database processing resource, phenotypic data relating to a health assessment of the animal and receiving in the database of the central database processing resource, genotypic data relating to the breed of the animal and the genetic background of the animal; and
   a communications network for reporting the analysis of the phenotypic data and genotypic data.

27. The apparatus of claim 26, including means for permitting a remote user of the database to pay for an analysis of the health profile and genetic screening tests through a computer network, and including a computer communication network for submitting the report to a remote user after receipt of the payment.

28. A computer-readable medium having stored thereon instructions for a computer to access the medium comprising:

instructions to access data on the medium;

a first database on the medium related to genotypic data of a non-human animal, a second database on the medium related to phenotypic data of the animal; and the computer-readable medium including instructions to analyze the first and second database, wherein the instructions are selected from the group consisting of predicting health, predicting disease probabilities, predicting disorder probabilities and longevity of the animal.

29. The medium as claimed in claim 28, wherein the phenotypic data includes biological laboratory test data relating to a health assessment of a the animal.

30. The medium of claim 29, including analysis data of the phenotypic and genotypic data related to the animal, and a report based on the analysis data.

31. The medium of claim 28, including data for permitting communication between a remote user and a central database processing resource through a computer network, data for permitting access through approved access codes, such data selectively including a credit card information of a user prior to providing a communication access to the database storage system of at least one of phenotypic or genotypic data.

32. A system for reporting the analysis of phenotypic data and genotypic data of a non-human animal comprising:

a computer based communications network, a computer at a central database processing resource provider to receive through the network, phenotypic data for the animal, the phenotypic data including physical characteristics and health assessment data, and genotypic data about the animal the genotypic data including genetic background, genomic mapping and genetic screening data, a screen for monitoring, using a computer, both the phenotypic data of the animal, and the genotypic data about the animal, a computer for analyzing the phenotypic data and the genotypic data based on predetermined characteristics, and a computer for receiving, through the network, the analysis.

33. The system of claim 32, including receiving in a database of a central database processing resource, phenotypic data relating to a health assessment of the animal and receiving in the database of the central data processing resource, genotypic data relating to the genomic map, genetic background, and genetic screening information about the animal.

34. The system of claim 32, including permitting a remote user of the network to pay for an analysis of phenotypic and genotypic data through the computer network, and including permitting the computer communications network to submit the report to the remote user after receipt of the payment.

* * * * *